US012558397B2

(12) United States Patent
Jo et al.

(10) Patent No.: US 12,558,397 B2
(45) Date of Patent: Feb. 24, 2026

(54) COMPOSITION FOR PREVENTION, AMELIORATION, OR TREATMENT OF URINATION-RELATED DISEASES COMPRISING CEPHALOTOCIN

(71) Applicants: KOREA RESEARCH INSTITUTE OF CHEMICAL TECHNOLOGY, Daejeon (KR); NATIONAL MARINE BIODIVERSITY INSTITUTE OF KOREA, Chungcheongnam (KR)

(72) Inventors: Seon Mi Jo, Gunsan-si (KR); Seung Hyun Jung, Cheonan-si (KR); Ki Hyun Kim, Chungcheongn-do (KR); Dae Sung Lee, Gunsan-si (KR); Dong Ho Woo, Daejeon (KR); Ye Ji Kim, Gangneung-si (KR); Chang hoon Choi, Daejeon (KR); Joung Wook Seo, Daejeon (KR)

(73) Assignees: KOREA RESEARCH INSTITUTE OF CHEMICAL TECHNOLOGY, Yuseong-gu (KR); NATIONAL MARINE BIODIVERSITY INSTITUTE OF KOREA, Seocheon-gun (KR)

( * ) Notice: Subject to any disclaimer, the term of this patent is extended or adjusted under 35 U.S.C. 154(b) by 679 days.

(21) Appl. No.: 18/045,047

(22) Filed: Oct. 7, 2022

(65) Prior Publication Data

US 2023/0190862 A1 Jun. 22, 2023

Related U.S. Application Data

(63) Continuation of application No. PCT/KR2021/004415, filed on Apr. 8, 2021.

(30) Foreign Application Priority Data

Apr. 9, 2020 (KR) ........................ 10-2020-0043255

(51) Int. Cl.
*A61K 38/095* (2019.01)
*A23L 33/18* (2016.01)
*A61P 13/00* (2006.01)

(52) U.S. Cl.
CPC ............ *A61K 38/095* (2019.01); *A23L 33/18* (2016.08); *A61P 13/00* (2018.01)

(58) Field of Classification Search
CPC ........ A23L 33/18; A61K 38/095; A61P 13/00
See application file for complete search history.

(56) References Cited

U.S. PATENT DOCUMENTS

| | | | | | |
|---|---|---|---|---|---|
| 2005/0232997 | A1* | 10/2005 | Nilsson | .................. | A61K 47/26 |
| | | | | | 514/6.9 |
| 2011/0237508 | A1* | 9/2011 | Amorij | ..................... | A61P 7/12 |
| | | | | | 514/10.9 |
| 2013/0164372 | A1* | 6/2013 | Imran | ..................... | A61L 29/16 |
| | | | | | 514/10.9 |

FOREIGN PATENT DOCUMENTS

| | | |
|---|---|---|
| JP | 6223377 B2 | 11/2017 |
| KR | 101581476 B1 | 12/2015 |
| KR | 102202346 B1 | 1/2021 |

OTHER PUBLICATIONS

Gruber et al., "Exploring bioactive peptides from natural sources for oxytocin and vasopressin drug discovery," Future Med Chem. Sep. 2012; 4(14). (Year: 2012).*
Baran, N., "Sensitive Periods, Vasotocin-Family Peptides, and the Evolution and Development of Social Behavior", Frontiers in Endocrinology, vol. 8, Article 189, Aug. 2017, 12 pp.
Glavas, M. et al., "Vasopressin and Its Analogues: From Natural Hormones to Multitasking Peptides, International Journal of Molecular Sciences", Int. J. Mol. Sci. 2022, 23, 3068, 30 pp.
Ishizuka, O et al., "Cold Stress and Urinary Frequency", Department of Urology and Lower Urinary Tract Symptoms, 2012, Blackwell Publishing Asia Pty Ltd, pp. 67-74.
Kim, Y. et al., "An Octopus-Derived Peptide with Antidiuretic Activity in Rats", Mar. Drugs, 2022, 20, 328, 13 pp.
Lawton S. et al., "Differences in Fluid, Electrolyte, and Energy Balance in C57BL/6J Mice (*Mus musculus*) in Metabolic Caging at Thermoneutral or Standard Room Temperatures" Journal of the American Association for Laboratory Animal Science, vol. 63, No. 2, Mar. 2024, pp. 190-200.
Pierce, m. et al., "A Comparison of the Ability of Leu8—and Pro8—Oxytocin to Regulate Intracellular Ca2+ and Ca2+− Activated K+ Channels at Human and Marmoset Oxytocin Receptors", Molecular Pharmacology, 95:376-385, Apr. 2019, The American Society for Pharmacology and Experimental Therapeutics, 10 pp.
Reich, G., "A new peptide of the oxytocin/vasopressin family isloted from nerves of the cephalopod *Octopus vulgaris*," Neuroscience Letters, 134, p. 191-194. 1992.
Goto, Y., "The Structure and Function of V1b Vasopressin Receptors," University of Birmingham, School of Biosciences, p. 1-262. Sep. 2009.

(Continued)

*Primary Examiner* — Jared Barsky
(74) *Attorney, Agent, or Firm* — Greenberg Traurig, LLP

(57) ABSTRACT

The present invention relates to a composition for the prevention, amelioration, or treatment of urination-related disases, comprising cephalotocin. The cephalotocin according to the present invention modulates oxytocin receptors and vasopressin receptors, and has the effect of reducing urine volume by promoting water reabsorption in the kidneys. This means that cephalotocin has a significant antidiuretic effect, and thus, the cephalotocin of the present invention can be variously used in the field of prevention, amelioration, or treatment of urinary disorders or urination-related diseases.

5 Claims, 5 Drawing Sheets

Specification includes a Sequence Listing.

(56) References Cited

OTHER PUBLICATIONS

Van Kesteren, R.E., "A vasopressin-related peptide in the mollusc *Lymnaea stagnails*: peptide structure, prohormone organization, evolutionary and fuctional aspects of Lymnaea conopressin," Progress in Brain Research, vol. 92, p. 47-57. 1992.

Arima, H. et al., "Central diabetes insipidus," Nagoya J. Med Sci, vol. 78, p. 349-357. 2016.

Kanda, A. et al., "Novel evolutionary lineages of the invertebrate oxytocin/vasopressin superfamily peptides and their receptors in the common octopus (*Octopus vulgaris*)," Biochem. J. vol 387, p. 85-91. 2005.

International Search report from corresponding PCT Application No. PCT/KR2021/004415, mailed Jul. 7, 2021.

* cited by examiner

【Figure 1】
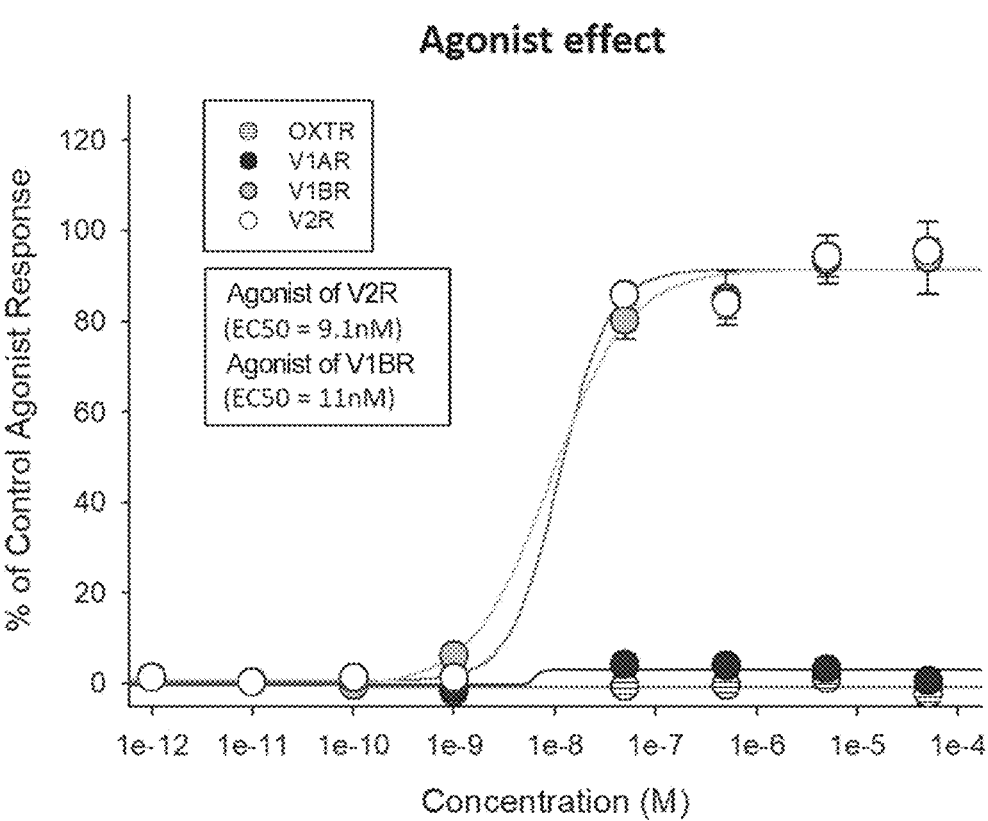

【Figure 2】
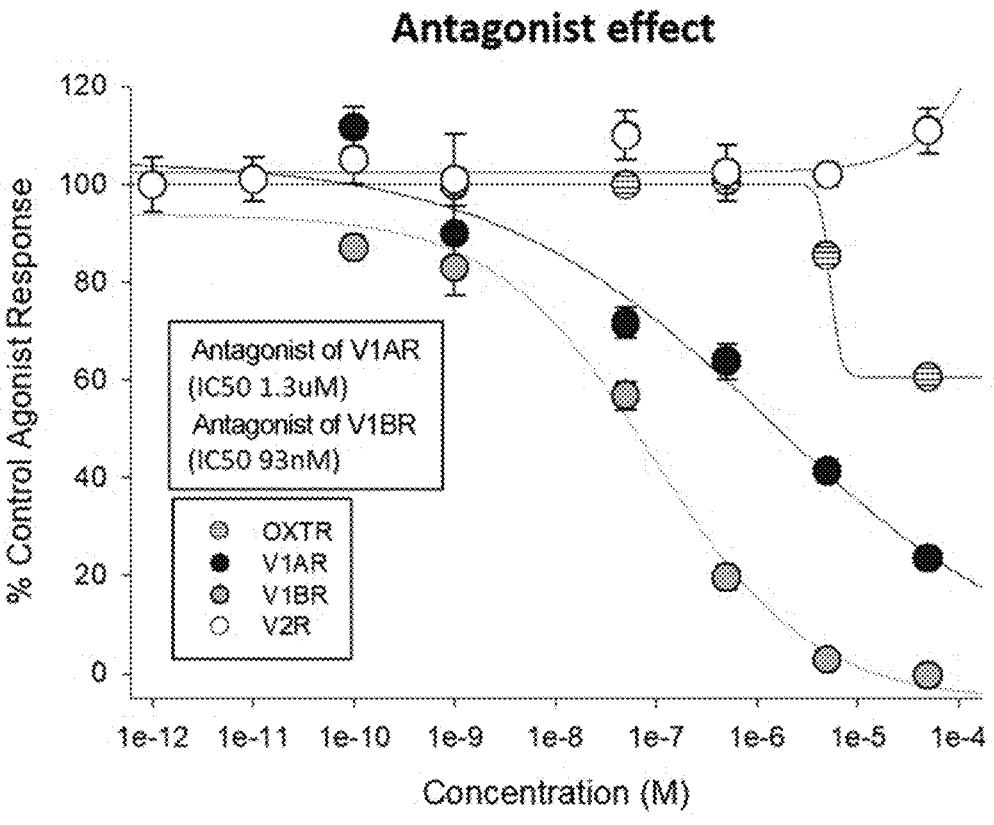

【Figure 3】
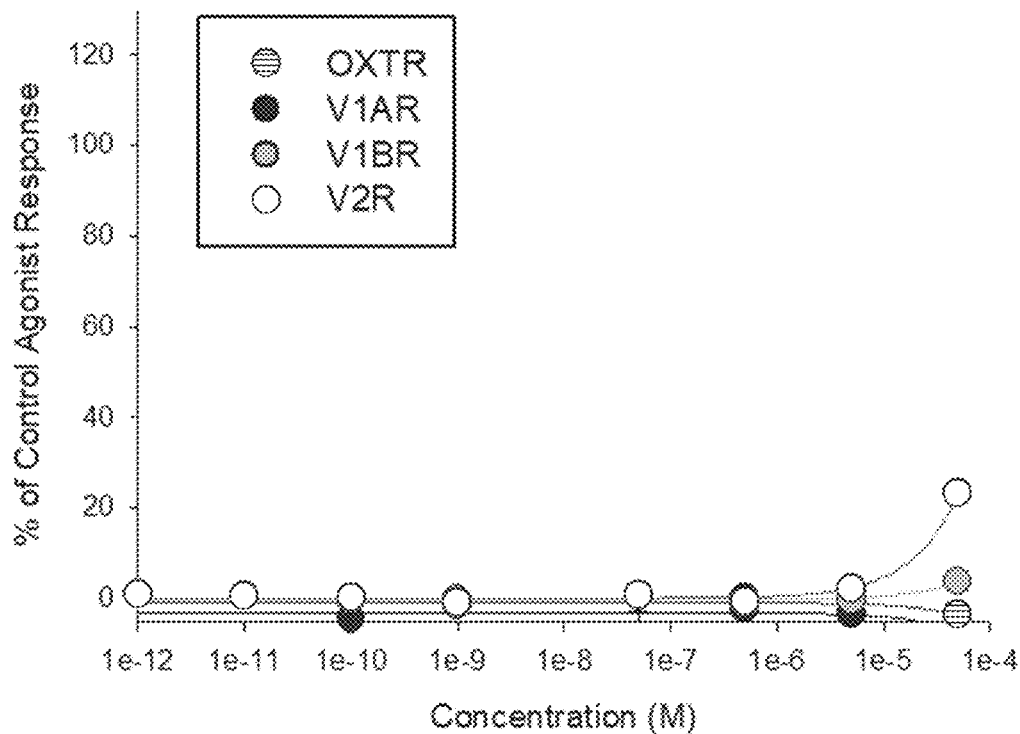

【Figure 4】
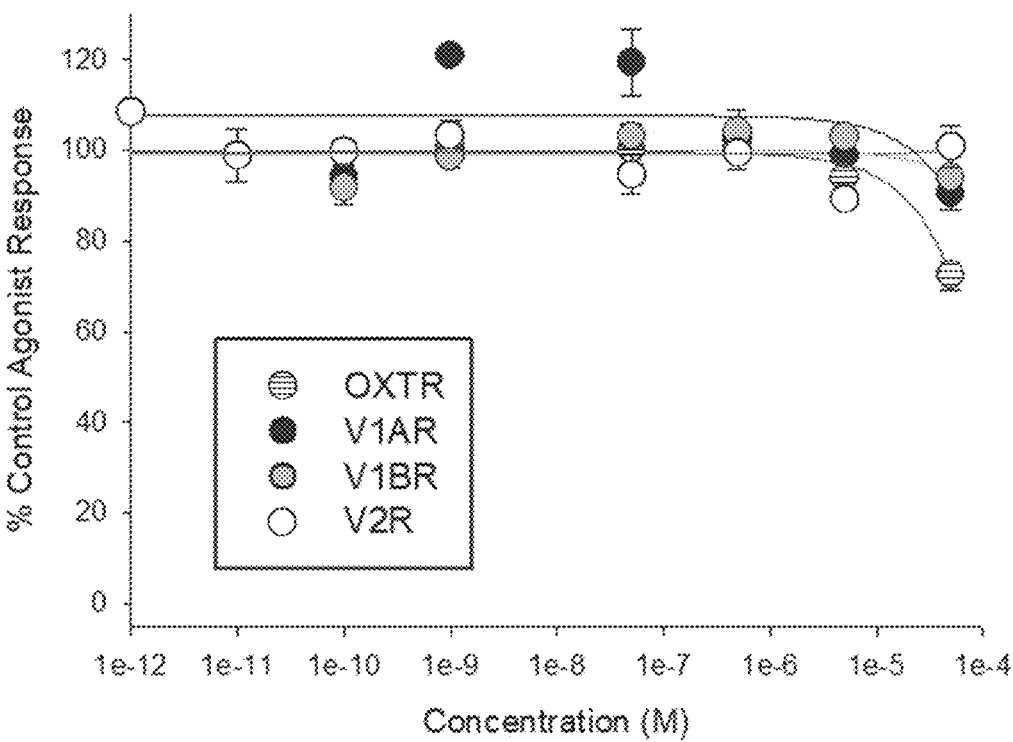

〖Figure 5〗
Urine volume (ml)
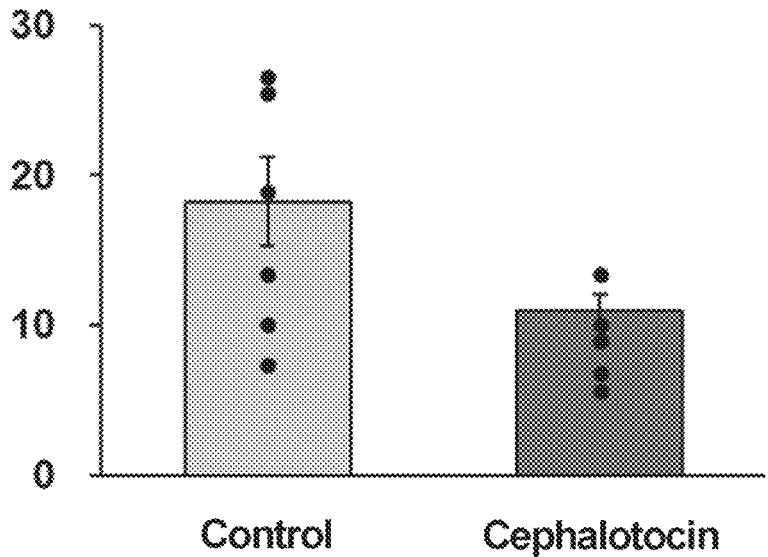
Urine osmolality (mOsm/kg)
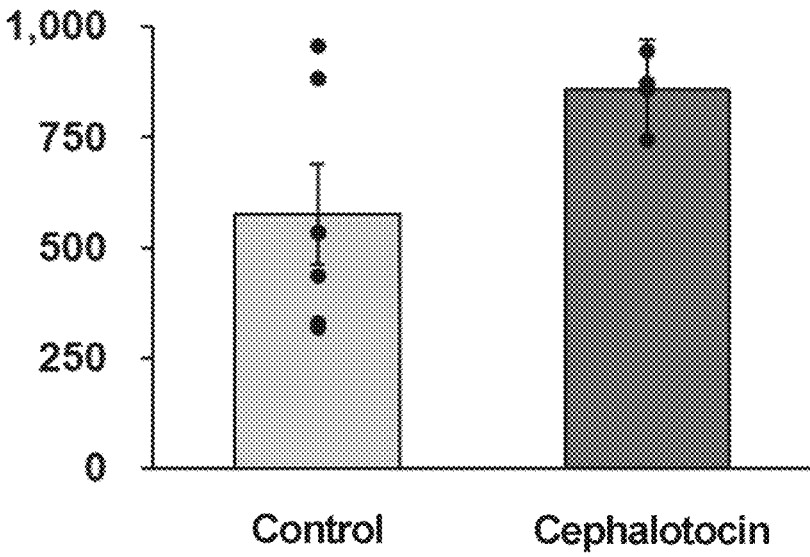

COMPOSITION FOR PREVENTION, AMELIORATION, OR TREATMENT OF URINATION-RELATED DISEASES COMPRISING CEPHALOTOCIN

CROSS REFERENCE TO RELATED APPLICATIONS

This application is the U.S. Continuation of International PCT Application No. PCT/KR2021/004415, filed Apr. 8, 2021, which claims the benefit of and priority to Korean Application No. 10-2020-0043255, filed Apr. 9, 2020, each of which are hereby incorporated by reference in their entirety.

REFERENCE TO AN ELECTRONIC SEQUENCE LISTING

The contents of the electronic sequence listing (OP-21005-PCT-US_MABIK1-1PCT.ST25.xml; Size: 1,812 bytes; and Date of Creation: Oct. 7, 2022) is herein incorporated by reference in its entirety.

TECHNICAL FIELD

The present invention relates to a composition for preventing, alleviating or treating urination-related diseases, including cephalotocin.

BACKGROUND ART

Vasopressin (Arginine Vasopressin) is a type of peptide hormone produced by the hypothalamus and secreted by the posterior pituitary gland and is widely known as an antidiuretic hormone. It is known that secretion is promoted when the osmotic concentration of body fluids is increased, and it is secreted into blood vessels and delivered throughout the body through blood. As a result, it promotes the reabsorption of water in the kidneys, reduces urine volume, and constricts the arteries, thereby increasing blood pressure. Further, its function as a neuropeptide that acts in the brain and regulates intimacy, sexual desire, and aggression toward others is being revealed.

Vasopressin acts through the vasopressin receptor. Humans have three vasopressin receptors, each made by different genes. They are called V1A (or V1) receptors, V1B (or V3) receptors, and V2 receptors, respectively. Depending on the type of each organ and cell in the human body, different receptors have different levels of expression. For example, the V1A receptor is expressed in vascular smooth muscle, platelets, hepatocytes, and fascia to be involved in vasoconstriction or platelet aggregation, and the V1B receptor is expressed in the anterior pituitary gland of the brain to be involved in the secretion of other hormones such as prolactin and endorphins. The V2 receptor is expressed on the basement membrane of the renal collecting duct and promotes water reabsorption through the water passage to exhibit an antidiuretic effect, and it is expressed in vascular endothelial cells to secrete vascular coagulation factor (vWF, Factor VIII) and is expressed in vascular smooth muscle to cause vasodilation. In addition, vasopressin may act on receptors for oxytocin, a hormone similar to vasopressin. For the EC50 value, which is the concentration at which vasopressin may activate 50% of each receptor, it is known that human V1A receptors have 0.24 nM, V1B receptors have 2.0 to 4.3 nM, V2 receptors have 0.05 nM, and oxytocin receptors have 8.3 to 15 nM.

Currently, several types of drugs that activate vasopressin and vasopressin receptors are commercially available and widely used. Each drug has different fields of application depending on how selectively it responds to which of the vasopressin/oxytocin receptors.

Synthetic vasopressin is used for the differential diagnosis of pituitary diabetes insipidus, pituitary or nephrogenic diabetes insipidus in humans, removal of intestinal gas (abdominal bloating, pretreatment of gallbladder imaging, pretreatment of pyelonephrography), and emergency treatment of esophageal variceal hemorrhage, and "lypressin", a vasopressin analog derived from pigs is also used for the prevention and control of symptoms of diabetes insipidus. "Desmopressin" modified with amino acids at a position of 1 and 8 of vasopressin activates the V2 receptor and is widely used for the treatment of nocturia symptoms related to primary nocturia in 5 years of age or older and polyuria at night in adults. In addition, "terlipressin," a vasopressin analog that selectively activates V1 receptors, is used for esophageal variceal hemorrhage and type 1 hepatic nephrotic syndrome, and another analog, "felypressin," is used as a vasoconstrictor. In addition, various analogs are still in the process of development. Various methods, such as subcutaneous injection, intramuscular injection, intravenous injection, continuous intravenous injection, oral administration (pill, powder, film) and nasal spray, are applied for the administration of these substances to the human body.

DISCLOSURE

Technical Problem

Accordingly, the present inventors completed the present invention by confirming that cephalotocin regulates oxytocin receptors and vasopressin receptors and promotes water reabsorption in the kidneys to reduce urine output as a result of conducting research on the treatment of urination-related diseases.

Accordingly, an object of the present invention is to provide a composition for preventing, alleviating or treating urination-related diseases including cephalotocin represented by the amino acid sequence of SEQ ID NO: 1 as an active ingredient.

Another object of the present invention is to provide an antidiuretic composition including cephalotocin represented by the amino acid sequence of SEQ ID NO: 1 as an active ingredient.

Still another object of the present invention is to provide a method for preventing or treating urination-related diseases, including step of administering an individual in need thereof with cephalotocin represented by the amino acid sequence of SEQ ID NO: 1.

Technical Solution

In order to achieve the above object, the present invention provides a pharmaceutical composition for preventing or treating urination-related diseases including cephalotocin represented by the amino acid sequence of SEQ ID NO: 1 as an active ingredient.

In addition, the present invention provides a food composition for preventing or alleviating urination-related diseases including cephalotocin represented by the amino acid sequence of SEQ ID NO: 1 as an active ingredient.

In addition, the present invention provides a pharmaceutical composition for antidiuresis including cephalotocin represented by the amino acid sequence of SEQ ID NO: 1 as are active ingredient.

In addition, the present invention provides a health functional food composition for anti diuresis including cephalotocin represented by the amino acid sequence of SEQ ID NO: 1 as an active ingredient.

In addition, the present invention provides a method for preventing or treating urination-related diseases, including step of administering an individual in need thereof with cephalotocin represented by the amino acid sequence of SEQ ID NO: 1.

Advantageous Effects

Cephalotocin according to the present invention regulates oxytocin receptors and vasopressin receptors and promotes water reabsorption in the kidneys, thereby reducing urine output. This means that cephalotocin has a significant antidiuretic effect, and the cephalotocin of the present invention can be used in various ways in the field of prevention, alleviation, or treatment of urinary diseases or urination-related diseases.

DESCRIPTION OF DRAWINGS

FIG. 1 is a view showing the results of confirming the receptor activation effect (agonist effect) of cephalotocin on the oxytocin receptor and the vasopressin receptor.

FIG. 2 is a view showing the results of confirming the receptor inhibitory effect (antagonist effect) of cephalotocin on the oxytocin receptor and the vasopressin receptor.

FIG. 3 is a view showing the results of confirming the receptor activation effect of octopressin on the oxytocin receptor and the vasopressin receptor.

FIG. 4 is a view showing the results of confirming the receptor inhibitory effect of octopressin on the oxytocin receptor and the vasopressin receptor.

FIG. 5 is a view showing the results of measurement of urine volume and osmolality according to cephalotocin treatment in experimental animals.

BEST MODE

Hereinafter, the present invention is described in detail.

According to an aspect of the present invention, the present invention provides a composition for preventing, alleviating or treating urination-related diseases, the composition including cephalotocin represented by the amino acid sequence of SEQ ID NO: 1 as an active ingredient.

According to another aspect of the present invention, the present invention provides a method for preventing or treating urination-related diseases, the method including step of administering an individual in need thereof with cephalotocin represented by the amino acid sequence of SEQ ID NO: 1.

In an embodiment of the present invention, the individual is an individual expected to develop a urination-related disease; diseased individuals; or an individual who has been determined to be cured but is not limited thereto.

As used herein, cephalotocin is a peptide belonging to the vasopressin/oxytocin superfamily. The present inventors analyzed the full-length genome and transcriptome information of previously published California two-spot octopus (*Octopus bimaculoides*) and the long arm octopus (*Octopus minor*) to confirm that they also have genes annotated with cephalotocin. The present inventors predicted that the active peptide portion of their cephalotocin had the same amino acid sequence as that of cephalotocin of *Octopus vulgaris*. Octopus-derived cephalotocin dealt with in the present invention differs from vasopressin by two amino acids and oxytocin by three amino acids, so it is self-evident that the effectiveness and effect of cephalotocin in mammals may also be known only through actual experiments.

In an embodiment of the present invention, the cephalotocin is preferably derived from at least one selected from the group consisting of the long arm octopus (*Octopus minor*), the giant Pacific octopus (*Enteroctopus dofleini*), the bigfin reef squid (*Sepioteuthis lessoninana*), the common octopus (*Octopus vulgaris*), the common octopus, the web-foot octopus (*Amphioctopus fangsiao*), the butterfly bobtail (*Sepiola birostrata*) and the Mimika bobtail squid (*Euprymna morsei*), more preferably *Octopus minor*.

The cephalotocin according to the present invention may be in a form in which the N-terminus or C-terminus is modified or protected with various organic groups in order to protect from proteolytic enzymes in vivo and to increase stability. That is, the C terminus of cephalotocin may not be particularly limited, as long as it is in a form that may be deformed to increase stability, but it may be preferably modified with a hydroxyl group (—OH) or an amino group (—NH$_2$). In addition, the N terminus of cephalotocin may not be particularly limited, as long as it is in a form that may be deformed to increase stability, but it may be preferably modified with a group selected from the group consisting of an acetyl group, a fluorenyl methoxycarbonyl (Fmoc) group, a formyl group, a palmitoyl group, a myristyl group, a stearyl group, and polyethylene glycol (PEG).

The cephalotocin may consist of the amino acid sequence of SEQ ID NO: 1 and includes a functional equivalent of the peptide. The "functional equivalent" refers to having at least 70% or more, preferably 80% or more, more preferably 90% or more, even more preferably 95% or more sequence homology with the amino acid sequence of SEQ ID NO: 1, as a result of addition, substitution or deletion of amino acids and refers to a protein having substantially the same physiological activity as the protein consisting of the amino acid sequence of SEQ ID NO: 1. In addition, for the cephalotocin of the present invention includes, not only a protein having its native amino acid sequence but also an amino acid sequence variant thereof are included in the scope of the present invention. A cephalotocin variant refers to a protein having a sequence different from the native amino acid sequence of cephalotocin by deletion, insertion, non-conservative or conservative substitution of one or more amino acid residues, or a combination thereof. Amino acid exchanges in proteins and peptides without entirely altering the activity of the molecule are known in the art. The cephalotocin or a variant thereof may be extracted from nature or prepared by a synthetic or genetic recombination method based on a DNA sequence.

In an embodiment of the present invention, the concentration of cephalotocin is preferably 0.1 to 10 mg/kg, more preferably 1 to 5 mg/kg, and more preferably 2 mg/kg.

In the present invention, urination-related disease refers to all kinds of abnormal conditions that occur in relation to the process of urination comprehensively, and it includes a variety of urination abnormalities, such as urinating too often, urinating for too long, or urinating involuntarily. Urination-related diseases usually occur when there is an abnormality in the bladder, prostate, or urethra.

In an embodiment of the present invention, the urination-related diseases preferably include at least one urination-related disease selected from the group consisting of diabetes insipidus, bed-wetting, enuresis, nocturia, polyuria, nocturnal polyuria, frequent urination, low bladder capacity, urinary incontinence, urinary urgency, neurogenic bladder, and overactive bladder.

Urinary incontinence is a disease in which urine comes out regardless of the will by losing the ability to control the urine. Urinary urgency is a disease in which the urge to urinate suddenly arises, and it may not be delayed. Enuresis is a disease in which a patient occurs twice or more to urinate at night. This may occur temporarily, or it may show persistent, uncomfortable symptoms as getting older.

The present inventors confirmed that cephalotocin modulates oxytocin receptors and vasopressin receptors and reduces urine output by promoting water reabsorption in the kidneys. This means that cephalotocin has a significant antidiuretic effect, and the cephalotocin of the present invention may be used in various ways in the field of prevention, alleviation, or treatment of urinary diseases or urination-related diseases.

In an embodiment of the present invention, the composition according to the present invention may further include one or more known ingredients having an effect of preventing, alleviating or treating urination-related diseases.

In an embodiment of the present invention, the composition of the present invention may be a pharmaceutical composition or a food composition.

When the composition is a pharmaceutical composition, it may further include a pharmaceutically acceptable carrier.

In the present invention, a pharmaceutically acceptable carrier means a carrier or diluent that does not stimulate the organism and does not inhibit the biological activity and properties of cephalotocin. Acceptable pharmaceutical carriers for compositions formulated as liquid solutions include sterile and biocompatible. Saline, sterile water, Ringer's solution, buffered saline, albumin injection, dextrose solution, maltodextrin solution, glycerol, ethanol and mixture including one or more of these components may be used. Other conventional additives such as antioxidants, buffers, and bacteriostats may be added as needed. In addition, diluents, dispersants, surfactants, binders and lubricants may be additionally added to form an injectable formulation such as an aqueous solution, suspension, emulsion, etc., pills, capsules, granules or tablets.

The pharmaceutical composition of the present invention may be administered through oral administration or parenteral administration. In the case of parenteral administration, it may be administered using intravenous administration, intraperitoneal administration, intramuscular administration, subcutaneous administration or local administration.

Suitable dosages of the pharmaceutical composition of the present invention vary according to factors such as the formulation method, administration method, age, weight, and gender of the target animal and patient, degree of disease symptoms, food, administration time, administration route, excretion rate and reaction sensitivity, and a normally skilled physician or veterinarian may readily determine and prescribe an effective dosage for the desired treatment.

Formulations for oral administration including the pharmaceutical composition of the present invention as an active ingredient include, for example, tablets, troches, lozenges, aqueous or emulsive suspensions, powders or granules, emulsions, hard or soft capsules, syrups or elixirs. For formulation into dosage forms such as tablets and capsules, binders such as lactose, saccharose, sorbitol, mannitol, starch, amylopectin, cellulose or gelatin, excipients such as dicalcium phosphate, disintegrants such as corn starch or sweet potato starch, lubricants such as magnesium stearate, calcium stearate, sodium stearylfumarate, or polyethylene glycol wax. In the case of a capsule formulation, it may further contain liquid carriers such as fatty oil in addition to the above-mentioned substances.

Formulations for parenteral administration including the pharmaceutical composition of the present invention as an active ingredient include an injection form such as subcutaneous injection, intravenous injection or intramuscular injection, a suppository injection method, or spraying such as an aerosol for inhalation through the respiratory tract, etc. In order to formulate an injectable formulation, the composition of the present invention may be mixed with water together with a stabilizer or buffer to prepare a solution or suspension, and these may be formulated for unit administration in ampoules or vials. In the case of formulation for spraying such as an aerosol, a propellant or the like may be combined with an additive so that the water-dispersed concentrate or wet powder is dispersed.

When the composition is a food composition, it may be used as a health functional food, a food additive or a dietary supplement. When used as a food additive, the cephalotocin may be added as it is, or it may be appropriately used according to a conventional method such as mixing with other foods or food ingredients.

In addition, the mixing of the additional active ingredients may be suitably changed depending on the purpose of use (prevention, health or therapeutic treatment), and it is preferably included in an amount of 0.001 to 99.9% by weight and more preferably 1 to 80% by weight based on the total weight of the food composition. When the content is less than 0.001% by weight, the efficiency of intake may be reduced. When it exceeds 99.9% by weight, there is difficulty in the formulation.

As a specific example, in the production of food or beverage, the cephalotocin of the present invention is added in an amount of 15% by weight or less, preferably 10% by weight or less, based on the raw material. However, when consumed for a long period of time for health and hygiene or health control, it may be added in an amount equal to or less than the above range, and since there is no problem in safety, the active ingredient may be used in an amount equal to or more than the above range. The type of the food is not particularly limited, but examples of the food to which the cephalotocin of the present invention may be added include meat, sausage, bread, chocolate, candy, snacks, confectionery, pizza, ramen, other noodles, gum, dairy products such as ice cream, various soups, beverages, teas, drinks, alcoholic beverages, vitamin complexes, and the like, and includes all health foods in the ordinary sense.

When the food composition of the present invention is prepared as a beverage, it may contain additional ingredients such as various flavoring agents or natural carbohydrates like conventional beverages. Examples of natural carbohydrate include monosaccharides such as glucose and fructose; disaccharides such as maltose and sucrose; natural sweeteners such as dextrin and cyclodextrin; and synthetic sweeteners such as saccharin and aspartame may be used. The natural carbohydrate is included in an amount of 0.01 to 10% by weight, preferably 0.01 to 0.1% by weight, based on the total weight of the food composition of the present invention.

The food composition of the present invention may include various nutrients, vitamins, electrolytes, flavoring agents, colorants, pectic acid and salts thereof, alginic acid and salts thereof, organic acids, protective colloidal thickeners, pH adjusters, stabilizers, preservatives, glycerin, alcohol, carbonation agent used in carbonic acid beverages, and the like and may include, but is not limited to, the pulp for the manufacture of natural fruit juices, fruit juice beverages and vegetable beverages. These components may be used independently or in combination. The additive ratio is not particularly limited, but it is preferably included in the range of 0.01 to 0.1% by weight based on the total weight of the food composition of the present invention.

In the case of long-term ingestion for the purpose of health and hygiene or health control, the food composition of the present invention may be taken for a long period of time because there is no problem in safety.

According to another aspect of the present invention, the present invention provides an antidiuretic composition including cephalotocin represented by the amino acid sequence of SEQ ID NO: 1 as an active ingredient.

In the present invention, antidiuresis refers to the action of reducing the amount of urine. The antidiuretic preferably reduces the amount of urine by promoting the reabsorption of water in the renal tubules to concentrate the urine rather than the action of inhibiting the excretion of wastes itself.

In an embodiment of the present invention, the composition of the present invention may be an antidiuretic pharmaceutical composition or a health functional food composition.

In an embodiment of the present invention, the composition according to the present invention may further include one or more kinds of known ingredients having an antidiuretic effect.

Modes of the Invention

Hereinafter, the present invention is described in more detail through examples. It is apparent to those of ordinary skill in the art that these examples are only for illustrating the present invention, and the scope of the present invention is not to be construed as being limited by these examples.

EXAMPLE 1. CONFIRMATION OF THE RECEPTOR MODULATING EFFECT OF CEPHALOTOCIN

Experiment Method

In this example, the oxytocin receptor and vasopressin receptor regulating the action of cephalotocin (CYF RNC PIG, SEQ ID NO: 1) was confirmed. Vasopressin receptors are divided into V1 and V2 types. The V1 receptor is present in vascular smooth muscle and increases intracellular calcium concentration and constricts blood vessels. In addition, the V2 receptor is present in the collecting tubule of the kidney, and it is known to increase the intracellular cAMP concentration and promote water reabsorption in the collecting duct.

Test of Oxytocin Receptor OXTR Activity/Inhibitory Effect by Cephalotocin

Recombinant human epithelial cells overexpressing human oxytocin receptor (Name of cell line: ECSV304) were cultured and treated with cephalotocin at different concentrations at room temperature. The change in intracellular calcium concentration induced by cephalotocin-oxytocin receptor binding was measured by calcium dye fluorescence imaging.

To confirm the receptor activation effect, the response to increasing the intracellular calcium concentration that oxytocin 1 µM may cause was taken as 100%, and the relative magnitude of the response induced when treated with cephalotocin alone without oxytocin was measured To confirm the receptor inhibitory effect, the response to increasing the intracellular calcium concentration that oxytocin 30 nM may cause was taken as 100% standard, and the relative magnitude of the response induced when treated with oxytocin 30 nM and cephalotocin simultaneously was measured.

Test of Vasopressin Receptor V1AR Activity/Inhibitory Effect by Cephalotocin Recombinant human vasopressin V1A receptor-overexpressing Chinese hamster ovary cells (cell line name: CHO) were cultured and treated with cephalotocin at different concentrations at room temperature, and the change in intracellular calcium concentration induced by cephalotocin-vasopressin V1A receptor binding was measured by the calcium dye fluorescence imaging method.

To confirm the receptor activation effect, the response to increasing the intracellular calcium concentration that vasopressin 1 µM may cause was taken as 100% standard, and the relative magnitude of the response induced when treated with cephalotocin alone without vasopressin was measured.

To confirm the receptor inhibitory effect, the response to increasing the intracellular calcium concentration that vasopressin 10 nM may cause was taken as 100% standard, and the relative magnitude of the response induced when treated with vasopressin 10 nM and cephalotocin simultaneously was measured.

Test of Vasopressin Receptor V1BR Activity/Inhibitory Effect by Cephalotocin Recombinant human vasopressin V1B receptor-overexpressing murine basophilic leukemia (cell line name: RBL) was cultured and treated with cephalotocin at different concentrations at room temperature, and the change in intracellular calcium concentration induced by cephalotocin-vasopressin V1B receptor binding was measured by the calcium dye fluorescence imaging method.

To confirm the receptor activation effect, the response to increasing the intracellular calcium concentration that vasopressin 0.1 µM may cause was taken as 100% standard, and the relative magnitude of the response induced when treated with cephalotocin alone without vasopressin was measured.

To confirm the receptor inhibitory effect, the response to increasing the intracellular calcium concentration that vasopressin 5 nM may cause was taken as 100% standard, and the relative magnitude of the response induced when treated with vasopressin 5 nM and cephalotocin simultaneously was measured.

Test of Vasopressin Receptor V2R Activity/Inhibitory Effect by Cephalotocin Recombinant human vasopressin V2 receptor-overexpressing Chinese hamster ovary cells (cell line name: CHO) were cultured and treated with cephalotocin at different concentrations at room temperature for 30 minutes, and intracellular cAMP concentration accumulated for 30 minutes by cephalotocin-vasopressin V2 receptor binding was measured by the HTRF fluorescence imaging method. To confirm the receptor activation effect, the response to increasing the intracellular cAMP concentration that vasopressin 1 nM may cause for 30 minutes was taken as 100% standard, and the relative magnitude of the response induced when treated with cephalotocin alone for 30 without vasopressin was measured. To confirm the receptor inhibitory effect, the response to increasing the intracellular cAMP concentration that vasopressin 0.03 nM may cause for 30 minutes was taken as 100% standard, and the relative magnitude of the response induced when treated with vasopressin 0.03 nM and cephalotocin simultaneously was measured.

The results of confirming the agonist or antagonist effect of cephalotocin on each receptor are shown in FIGS. 1 and 2, respectively.

Comparative Example

In the same manner, as described above, an experiment was performed to confirm whether octopressin derived from *Octopus vulgaris,* which is a member of the same vasopressin family, has the same effect as cephalotocin. The results confirming the regulatory effect on the receptors OXTR, V1AR, V1BR and V2R by *Octopus vulgaris* octopressin are shown in FIGS. 3 and 4, respectively.

Experiment Result

As shown in FIG. 1, it was confirmed that cephalotocin activates the V2 receptor (EC50=9.1 nM) and the V1B receptor (EC50=11 nM). In addition, as shown in FIG. 2, it was confirmed that when the concentration of cephalotocin was increased, the activity of the V1A receptor was inhibited (IC50=1.3 μM). It was confirmed that cephalotocin also inhibits the V1B receptor (IC50=93 nM) in the presence of vasopressin nearby. Therefore, when cephalotocin is treated at a concentration of about 10 nM, it is predicted that only the V2 receptor is selectively activated and hardly acts on other receptors.

As shown in FIGS. 3 and 4, it was confirmed drat octopressin belonging to the vasopressin family does not regulate human octopressin receptors and vasopressin receptors.

The above results indicate that the activation or inhibitory of oxytocin receptors and vasopressin receptors may be regulated by controlling the concentration of cephalotocin. In addition, the octopressin results indicate that the regulatory effects on the oxytocin receptor and the vasopressin receptor are different, even if they belong to the vasopressin family.

EXAMPLE 2. CONFIRMATION OF ANTIDIURETIC EFFECT OF CEPHALOTOCIN

Twelve 6-week-old male SD rats (Sprague-Dawley rats) weighing 197 g to 218 g were purchased and acclimatized in a new breeding environment for seven days, and then used in the antidiuretic effect experiment.

The animal experiments in this experiment were conducted in accordance with the Korea Institute of Toxicology's standard work guidelines, Laboratory Animal Act, and the Laboratory Animal Care and Use Guide. For rats, feeding was stopped only 20 hours before the experiment, but drinking enough water was allowed freely.

The prepared rats were divided into two groups, and six mice were injected with cephalotocin represented by the amino acid sequence of SEQ ID NO: 1, and the remaining six mice were injected with physiological saline as a control group. The cephalotocin is prepared in the form of an injection solution, and the cephalotocin injection solution (0.1 mg/ml) is prepared by dissolving synthetic cephalotocin powder at 10 mg/ml in distilled water (about 10 mM) and diluting it 100 times in physiological saline. For injection, the rat was confined and fixed in a transparent plastic restrain; frame, and their tails were wiped with an alcohol swab to disinfect. Thereafter, they were administered once to the tail vein at the rate of 1 ml per 1 kg of the rat's body weight.

After intravenous injection, the rats were placed one by one in a cylindrical metabolic cage with a wire mesh bottom and placed for 22 hours from 10:30 am to 8:30 am the next day. In the metabolic cage, only water was provided without feeding so that the rats could drink enough water. Urine from each rat immediately flowed through the slanted floor below the metabolic cage wire mesh upon discharge and was collected in 50 ml plastic tubes. The volume and osmolality of urine collected for 22 hours were measured and the average value of the cephalotocin-administered group was compared with the average value of the control group, and the results are shown in FIG. 5.

As shown in FIG. 5, the urine volume of the control group injected with physiological saline was 18.25 ml. On the other hand, the urine volume of the cephalotocin-treated group was 11 ml, which was reduced by about 40% compared to the control group. In addition, the cephalotocin-treated group had an average urine osmolality of 858 mOsm/kg, which was increased by about 49% compared to the control group (576 mOsm/kg). The above results indicate that cephalotocin has an excellent effect on reducing urine volume and that cephalotocin reduces urine volume by promoting water reabsorption in the kidneys to concentrate urine, not by inhibiting waste excretion itself.

Overall, the present inventors confirmed that cephalotocin regulates oxytocin receptors and vasopressin receptors and promotes water reabsorption in the kidneys to reduce urine output. This means that cephalotocin has a significant antidiuretic effect, and thus the cephalotocin of the present invention may be used in various ways in the field of preventing, alleviating or treating urinary diseases or urination-related diseases.

Hereinafter, the present invention will be described in more detail through formulation examples. The formulation examples are only for illustrating the present invention, and the scope of the present invention is not to be construed as being limited by the formulation examples.

Hereinafter, the present invention is described in more detail through formulation examples. The formulation examples are only for illustrating the present invention, and the scope of the present invention is not to be construed as being limited by the formulation examples.

Formulation Example 1. Preparation of Pharmaceutical Composition 1-1. Preparation of Powders
 20 mg of cephalotocin
 100 mg of lactose
 10 mg of talc
 Powders are prepared by mixing the above ingredient and filling them in airtight bags
1-2. Preparation of Tablets
 10 mg of cephalotocin
 100 mg of cornstarch
 100 mg of lactose
 2 mg of magnesium stearate
 The above ingredients are mixed, and

Tablets are prepared by mixing the above ingredient and tableting according to a conventional manufacturing method of tablets.

1.-3. Preparation of Capsules 10 mg of cephalotocin 3 mg of crystalline cellulose 14.8 mg of lactose 0.2 mg of magnesium stearate Capsules are prepared by mixing the above ingredient and filling them in gelatin capsules according to a conventional manufacturing method of capsules.

1-4. Preparation of Injections 10 mg of cephalotocin 180 mg of mannitol 2974 mg of sterile distilled water for injection 26 mg of $Na_2HPO_42H_2O$ It is prepared in the content of the above ingredients per 1 ampoule (2 ml) according to a conventional manufacturing method of injections.

1-5. Preparation of Liquids 20 mg of cephalotocin 10 g of isonierized sugar 5 g of mannitol Purified water appropriate amount According to a conventional manufacturing method of liquids, each component is added to purified water to dissolve, an appropriate amount of lemon flavor is added, the above components are mixed, purified water is added, the whole is adjusted to 100 ml by adding purified water, and then filled in a brown bottle followed by sterilization to prepare a solution.

Above, specific parts of the present invention have been described in detail, it is clear for those of ordinary skill in the art that these specific descriptions are only preferred embodiments, and the scope of the present invention is not limited thereby. Accordingly, it is intended that the substantial scope of the present invention be defined by the appended claims and their equivalents.

---

SEQUENCE LISTING

```
Sequence total quantity: 1
SEQ ID NO: 1          moltype = AA  length = 9
FEATURE               Location/Qualifiers
source                1..9
                      mol_type = protein
                      organism = Octopus vulgaris
SEQUENCE: 1
CYFRNCPIG                                              9
```

---

The invention claimed is:

1. A method for alleviating or treating a urination-related disease, the method comprising:

administering to an individual in need thereof a composition comprising an effective amount of a cephalotocin represented by an amino acid sequence of SEQ ID NO: 1, wherein the effective amount induces antidiuresis in said individual, wherein the urination related disease includes at least one of diabetes insipidus, bedwetting, enuresis, nocturia, polyuria, nocturnal polyuria, frequent urination, low bladder capacity, urinary incontinence, urinary urgency, neurogenic bladder, and overactive bladder.

2. The method of claim 1, wherein the cephalotocin has a concentration of 0.1 mg/ml to 10 mg/ml.

3. The method of claim 1, wherein the composition is a pharmaceutical composition, a food composition, a health functional food composition, a food additive composition or a dietary supplement composition.

4. A method for antidiuresis, the method comprising:

administering to an individual in need thereof a composition comprising a cephalotocin represented by an amino acid sequence of SEQ ID NO: 1, wherein the effective amount induces said antidiuresis in said individual.

5. The method of claim 4, wherein the composition is a pharmaceutical composition, a food composition, a food additive composition, a dietary supplement composition, or a health functional food composition.

* * * * *